(12) United States Patent
Calvert et al.

(10) Patent No.: US 8,546,593 B2
(45) Date of Patent: Oct. 1, 2013

(54) METHODS AND COMPOSITIONS FOR NOVEL LIQUID CRYSTAL DELIVERY SYSTEMS

(75) Inventors: Richard Peter Curtis Calvert, Safety Harbor, FL (US); Charles D. Cappuccino, Kutztown, PA (US); James David Mosbaugh, Tampa, FL (US); Edmund L. Phelan, Killingworth, CT (US)

(73) Assignee: Copperhead Chemical Company, Inc., Tamaqua, PA (US)

( * ) Notice: Subject to any disclaimer, the term of this patent is extended or adjusted under 35 U.S.C. 154(b) by 69 days.

(21) Appl. No.: 12/906,744

(22) Filed: Oct. 18, 2010

(65) Prior Publication Data

US 2011/0301237 A1 Dec. 8, 2011

Related U.S. Application Data

(60) Provisional application No. 61/252,296, filed on Oct. 16, 2009.

(51) Int. Cl.
*C07C 51/00* (2006.01)

(52) U.S. Cl.
USPC .......................................... 554/156; 514/547

(58) Field of Classification Search
USPC .......................................... 554/156; 514/547
See application file for complete search history.

(56) References Cited

PUBLICATIONS

Chem. Abtstr of DE19751150, Oct. 1998.*

* cited by examiner

*Primary Examiner* — Deborah D Carr
(74) *Attorney, Agent, or Firm* — Beck & Thomas, P.C.

(57) ABSTRACT

Methods of making a liquid crystal mixture essentially comprised of at least one fatty acid ester or fatty acid, at least one polyhydric solvent, and at least one alkali reactant. The resultant mixture includes at least one fatty acid ester or fatty acid, at least one polyhydric solvent, and at least one salt of said fatty acid ester or fatty acid. The resultant mixture exhibits enhanced stability and aqueous solubility of fatty acids and fatty acid esters. When medium chain fatty acid monoglycerides are used in the method, the resultant mixture exhibits antimicrobial efficacy.

18 Claims, 3 Drawing Sheets

Microbiology Study Report NG1644

Results

| Microorganism | Sample | Contact Time | CFU/ml |
|---|---|---|---|
| Φ6 | C33 Polyglycercol | Time Zero | 5.10E+07 |
| | | 10 Mintues | < 100 |

Microbiology Study Report NG1644

Results

| Microorganism | Sample | Contact Time | CFU/ml |
|---|---|---|---|
| Φ6 | C33 Polyglycercol | Time Zero | 5.10E+07 |
| | | 10 Mintues | < 100 |

Note: Non-detects (< 100 CFU/ml) are presented as zero on this chart.

Suspension Time-Kill Study Report

Results for S. aureus 6538

| Microorganism | Test Substance | Contact Time | CFU/ml | Percent Reduction | Log Reduction |
|---|---|---|---|---|---|
| S. aureus 6538 | PC-32 | Time Zero | 5.55E+06 | N/A | N/A |
| | | 1 Minute | 5.00E+03 | 99.909910% | 3.05 |
| | | 10 Minutes | < 50 | > 99.999099% | > 5.05 |
| | | 60 Minutes | < 50 | > 99.999099% | > 5.05 |

FIGURE 3

Suspension Time-Kill Study Report

Results for S. aureus 6538

| Microorganism | Test Substance | Contact Time | CFU/ml | Percent Reduction | Log Reduction |
|---|---|---|---|---|---|
| S. aureus 6538 | PG-2 6/10/10 | Time Zero | 7.90E+06 | N/A | N/A |
| | | 1 Minute | < 50 | > 99.999367% | > 5.20 |
| | | 10 Minutes | < 50 | > 99.999367% | > 5.20 |
| | | 60 Minutes | < 50 | > 99.999367% | > 5.20 |
| | MEDOV 3 B 6/11/10 | Time Zero | 7.60E+06 | N/A | N/A |
| | | 1 Minute | 1.05E+07 | None | None |
| | | 10 Minutes | 7.55E+06 | 0.657895% | 0.00 |
| | | 60 Minutes | 1.40E+07 | None | None |
| | MEDOV 5 B 6/11/10 | Time Zero | 7.60E+06 | N/A | N/A |
| | | 1 Minute | 1.30E+07 | None | None |
| | | 10 Minutes | 2.44E+07 | None | None |
| | | 60 Minutes | 2.22E+07 | None | None |
| | MEDOV 6 B 6/11/10 | Time Zero | 7.60E+06 | N/A | N/A |
| | | 1 Minute | 8.45E+06 | None | None |
| | | 10 Minutes | 7.35E+06 | 3.289474% | 0.01 |
| | | 60 Minutes | 7.65E+06 | None | None |

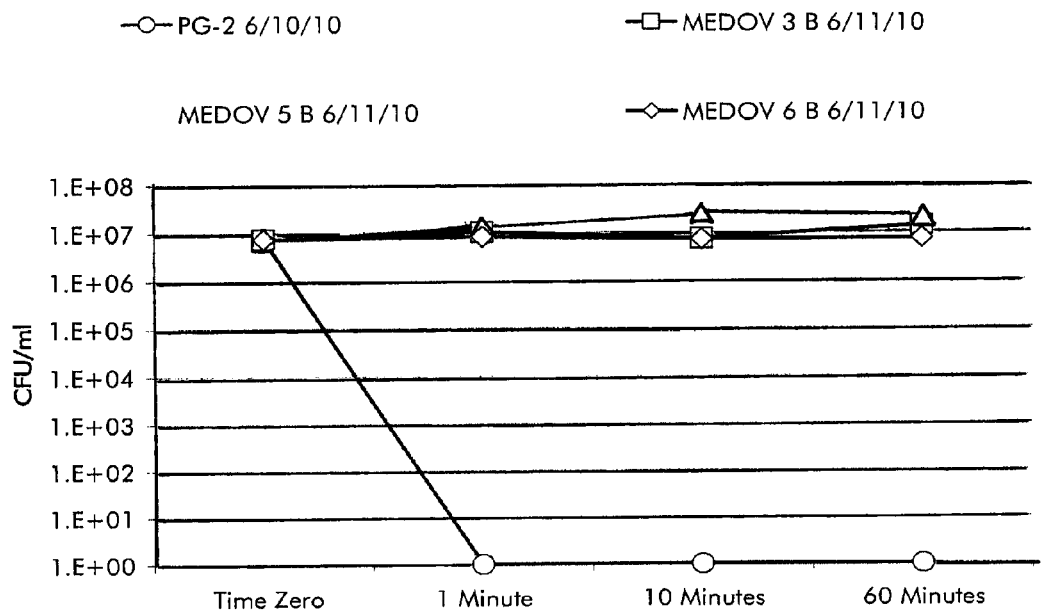

METHODS AND COMPOSITIONS FOR NOVEL LIQUID CRYSTAL DELIVERY SYSTEMS

CROSS-REFERENCE TO RELATED APPLICATIONS

This application claims priority to provisional patent application Ser. No. 61/252,296, filed Oct. 16, 2009.

FIELD OF THE INVENTION

The present invention relates generally to the preparation of a liquid crystal mixture comprised of a lipid or combination of lipids contained within an essentially anhydrous system. More specifically, the present invention relates to a novel delivery system wherein lipids with relatively low solubility are organized into discrete liquid crystal arrays within an essentially anhydrous, polyhydric solvent via the controlled hydrolysis of said lipid component. Even more specifically, the present invention relates to a process of manufacturing a composition comprised of liquid crystals of monoesters or monoglycerides and salts thereof, in a polyhydric alcohol medium via partial saponification of the lipid component via treatment with a reactant. In particular, the present invention relates to a process to manufacture a novel liquid crystal mixture composition comprised of a stable, highly concentrated, medium chain length fatty acid esters and ester salts contained within a polyhydric alcohol medium, essentially free of water but highly soluble therein that exhibits potent, broad spectrum antimicrobial efficacy.

BACKGROUND OF THE INVENTION

The use of antimicrobial compositions to help treat, prevent or control diseases of man and other animals is an integral part of modern medicine. Topical antimicrobial compositions are commonly used to help prevent the spread of disease from animals to man, from man to animals and between animals. Topical antimicrobial compositions are ubiquitous throughout modern society and are conveniently available, many times free of charge, in areas such as shopping centers, schools, and other public areas. Topical antimicrobial products may be in the form of lotions, gels, soap and shampoo, and other solutions; in the form of wipes or pads; or present as embedded in certain polymers or plastics.

The preservation of the active functions of ingredients (i.e., antibacterial, emollient, moisturizing, humectants, exfoliating) in complex systems is often problematic. That is, many active, therapeutic agents (especially those from natural origins) can be over-emulsified such that the benefit of the ingredient may be lost. For example, glyceryl monolaurate (GML) is a known, potent antimicrobial agent. However, it has very low solubility and is problematic is many aqueous and lipid based systems. Attempts to use GML in formulations via the addition of emulsifiers, however, typically result in a loss of desired product efficacy of GML, namely antimicrobial properties.

Topical antimicrobials have been shown to be effective in destroying bacteria, viruses, and certain fungi when applied appropriately. Typically, topical antimicrobials are applied directly to the skin or to surfaces wherein potential infective microorganisms may reside and present potential for transference from one animal to another.

In the United States, antimicrobial ingredients and products are governed by the US Food and Drug Administration (FDA) and the Environmental Protection Agency (EPA) depending upon the type of chemicals and intended use. The EPA provides regulatory guidance pursuant to the Federal Insecticide, Fungicide and Rodenticide Act (FIFRA) of 1947. Under FIFRA, no one may sell, distribute, or use a pesticide unless it is registered by the EPA, or it meets a specific exemption as described in the regulations. Registration includes approval by the EPA of the pesticide's label, which must give detailed instructions for its safe use. The EPA must classify each pesticide as either "general use," "restricted use," or both. "General use" pesticides may be applied by anyone, but "restricted use" pesticides may only be applied by certified applicators or persons working under the direct supervision of a certified applicator. Because there are only limited data for new chemicals, most pesticides are initially classified as restricted use. Applicators are certified by a state if the state operates a certification program approved by the EPA.

Antimicrobial ingredients and products intended for use on or in conjunction with animals, such as humans, fall under the jurisdiction of the FDA. The FDA considers the control of microorganisms found on the skin of individuals important to public health. The potential for the transmission of opportunistic pathogens to oneself or to others is significant, in the home, in institutional and commercial settings, as well as in healthcare settings. The risk of infection or acquisition of disease from the transmission of microorganisms can be correlated to specific tasks in all of these settings. The exposure and, consequently, the risk to populations of varying susceptibilities determine the ingredient performance desired and the attributes necessary to mitigate the risk.

The FDA, in 1978, found that the reduction of flora, both transient and resident, has been sufficiently supported to be considered a benefit. The agency has embraced the reduction of skin flora by a pre-specified amount as a valid surrogate end-point for the efficacy of topical over-the-counter (OTC) antimicrobial products. The Industry Coalition has concluded that the log reductions for non-professional antibacterial products are appropriate as cited by FDA in the Jun. 17, 1994 Tentative Final Monograph, 59 Fed. Reg. 31402 (TFM) (i.e., 2 $\log_{10}$), as long as standardized ASTM methods (with neutralization of all sampling fluids) are employed in the Final Monograph. In addition, the FDA mandates that topical antibacterial products should be effective the first time they are used, and effectiveness should be demonstrated after a single wash.

Per the FDA, today's generation of topical OTC antimicrobial products provide a public health benefit by reducing bacteria on skin. Such products are formulated with active ingredients that have the capability of reducing transient or resident organism populations with greater effectiveness and efficiency than can be achieved through the use of non-antimicrobial products. This additional reduction translates to risk reduction in the transmission of potentially pathogenic organisms and in the potential for disease acquisition (Breneman et al. 1998; Rose and Haas 1999).

In general, topical OTC antimicrobial products are designed to provide a prophylactic (i.e., preventive) benefit rather than a therapeutic benefit. The risks that are mitigated by topical OTC antimicrobial products are due to the acquisition of disease or illness from the transmission of transient organisms from oneself, others, or from environmental sources (e.g., fomites). In some cases reduction of resident flora may also be desirable (e.g., impetigo, eczema). These product attributes fully support the current OTC drug indication of "to decrease bacteria on skin" and translate into tangible public health benefits such as reductions in: the incidence of diarrhea; in skin/eye diseases; in illness rates (e.g., self-reported upper respiratory symptoms and secondary transmission of gastrointestinal illness); and in absenteeism due to infectious disease (e.g., colds, flu, gastrointestinal disease).

Topical OTC antimicrobial products are currently available in many forms that may or may not require a water rinse. Products used without water rinse include lotions, gels, sprays, liquids, and solid sticks. Products that require a water rinse include bars, shampoos, and soaps. Recently, solid wipe products have become popular and come in a variety of embodiments. These products usually contain a single antimicrobial ingredient. The type of composition is typically predicated by the application and includes aqueous, non-aqueous, oil in water, and water in oil emulsions.

There are many types of antimicrobial compositions that are generally recognized as safe (GRAS) include, but not limited to, ethyl alcohol, isopropyl alcohol, 2,4,4'-Trichloro-2'-hydroxydiphenyl ether (triclosan), benzalkonium chloride, benzethonium chloride, benzoic acid, benzyl alcohol, bromochlorophene, chlorophene, didecyldimonium chloride, lauritrimonium chloride, myristalkonium saccharinate, shilkonin, sodium capryloamphoacetate, p-tertarylphenol, phenol, phenoxyethanol, etc. Also listed are both monoesters of edible fatty acids and polyhydric alcohols such as glycerol monolaurate and short to medium chained saturated fatty acids such as caprylic, capric, and lauric acids. In particular, the glycerol monoester of lauric acid (glycerol monolaurate or monolaurin) in combination with a chelating agent such as lactic acid is reported to be an effective antimicrobial system.

Even though glycerol monolaurate has been shown to be an effective broad range antimicrobial agent, low solubility and the formation of microcrystalline structures in situ have limited its use in applications. Glycerol monolaurate is typically used in concentrations in commercial formulations between 1-2%. Even at such low concentrations, formulations containing glycerol monolaurate are unstable such that the use of surfactants, emulsifiers, or other stabilizing agents is required.

Attempts to increase the solubility of glycerol monolaurate, and other fatty acids esters, diglycerides, triglycerides, etc. has been the focus of much research and development. It has been found by the inventors herein that many of the common emulsifying mechanisms, for example the use of surfactants and emulsifiers with various HLB values and combinations thereof, can render the active ingredient ineffective. That is, the act of emulsifying glycerol monolaurate with traditional emulsifiers results in a non-antimicrobial product. Thus the prior art has encountered a long-standing problem when attempting to include such anti-microbial agents as glycerol monolaurate at substantial concentrations while maintaining its anti-microbial effectiveness. The present invention addresses that long-standing problem by providing formulations of highly soluble, stable liquid crystal mixture of biologically active fatty acid esters (salts and/or glycerol(s)) in an anhydrous polyhydric alcohol system in which the anti-microbial action of the fatty acid esters is maintained. The present invention further provides for methods for the generation of such formulations.

SUMMARY OF THE INVENTION

The present invention relates to a method of manufacturing a stable, highly concentrated liquid crystal mixture of fatty acid esters (glycerol and/or salt esters) by the partial saponification of said fatty acid esters in situ in the presence of at least one polyhydric alcohol solvent. The method produces a composition that greatly enhances the solubility and efficacy of biologically active medium chain fatty acid esters. The antimicrobial activity of the fatty acid esters is maintained by employing the methods of the present invention. Other properties native to the fatty acid esters (e.g., stability, penetration of skin layers) are also preserved and in some cases may be enhanced through employing the presently inventive process.

To be useful in as wide a range of products as possible and to improve and innovate the use of esters, the fatty acid ester mixtures of the present invention are preferably stable, present in high concentration in the formulation, and be non-partitioned by the process of preparation. Accordingly, one benefit of the invention is to provide a wide range of stable, soluble mixtures of fatty acid esters with concentrations ranging from about 10% to more than 90%. The viscosity of the formulation may range from free flowing liquid to a thick paste, and the density can be altered to make more the formulation compatible with aqueous and non-aqueous products.

In certain presently preferred embodiments, the present invention involves bringing at least one fatty acid ester with a carbon chain length of between $C_6$-$C_{32}$, or combinations thereof, into direct contact with at least one polyhydric alcohol. This mixture is heated to a temperature in excess of the melting point of said ester. A specific amount of alkaline reactant is then added directly to the heated mixture, resulting in hydrolysis of a portion of said fatty acid ester. This solution is then mixed in so that a clear, liquid crystal matrix of the fatty acid ester is formed. The liquid crystal mixture is dynamic and the crystalline morphology depends upon the concentration of ester and temperature. In other presently preferred embodiments, the method may be modified such that at least one fatty acid ester is combined with at least one polyhydric alcohol, and an alkali reactant together in a single mixture which is then heated to produce the liquid crystal mixture of the present invention.

The compositions made by the disclosed methods herein are then able to be used as potent, stable microbiocides, preservatives, disinfectants, sanitizers, fungicides, and other antimicrobial applications. Said composition may be manufactured to be generally regarded as safe (GRAS) and edible.

The present invention thus provides a stable, liquid crystal mixture comprised of at least one fatty acid ester, at least one polyhydric alcohol, and at least one fatty acid ester salt. The present invention further provides for methods for the preparation of said stable liquid crystal mixture by the partial saponification of a fraction of said fatty acid ester by adding an alkaline reactant. The present invention provides a liquid crystal composition that is essentially free of water. The compositions of the present invention possess increased solubility over the prior art containing medium chain fatty acid esters, and specifically glycerol monoesters. The compositions of the present invention preferably include a liquid crystal mixture that exhibits antimicrobial properties, also having decreased incidence of problematic crystallization upon formulation in various vehicles. The present invention further provides for topical formulations containing a liquid crystal mixture of medium chain glycerol monoesters that is capable of quick kill of microorganisms.

BRIEF DESCRIPTION OF THE DRAWINGS

The following figures set forth various embodiments of the present invention:

FIG. 3 shows results from suspension time kill testing performed on a stable liquid crystal mixture of the antimicrobial of the present invention compared to 3 non-liquid crystal emulsions of glycerol monolaurate made with common emulsifiers and carried in mineral oil.

DETAILED DESCRIPTION OF PREFERRED EMBODIMENTS

Figure 1:
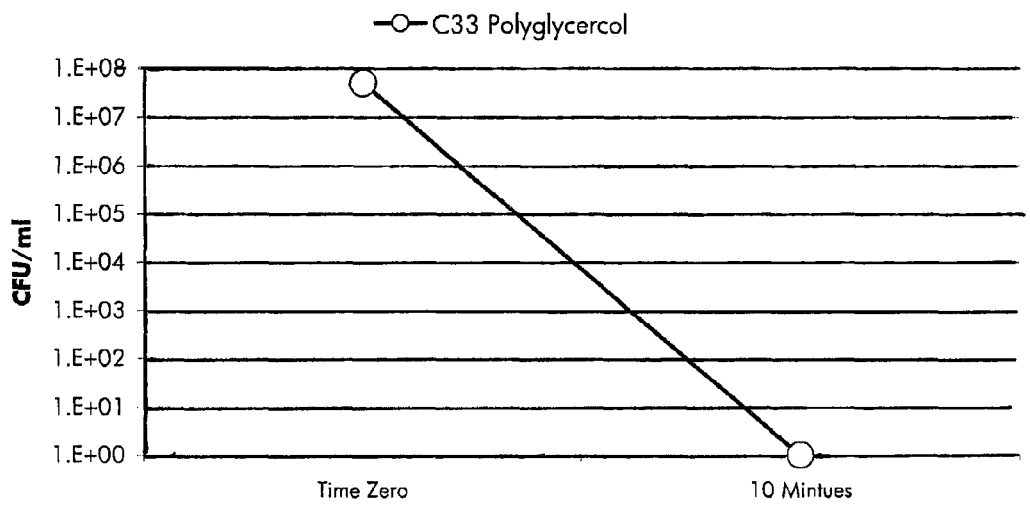
FIG. 1 shows results from quantitative suspension time-kill test performed with Φ6 Phages (NB10Y) contained in tryptic broth growth medium.
Figure 2:
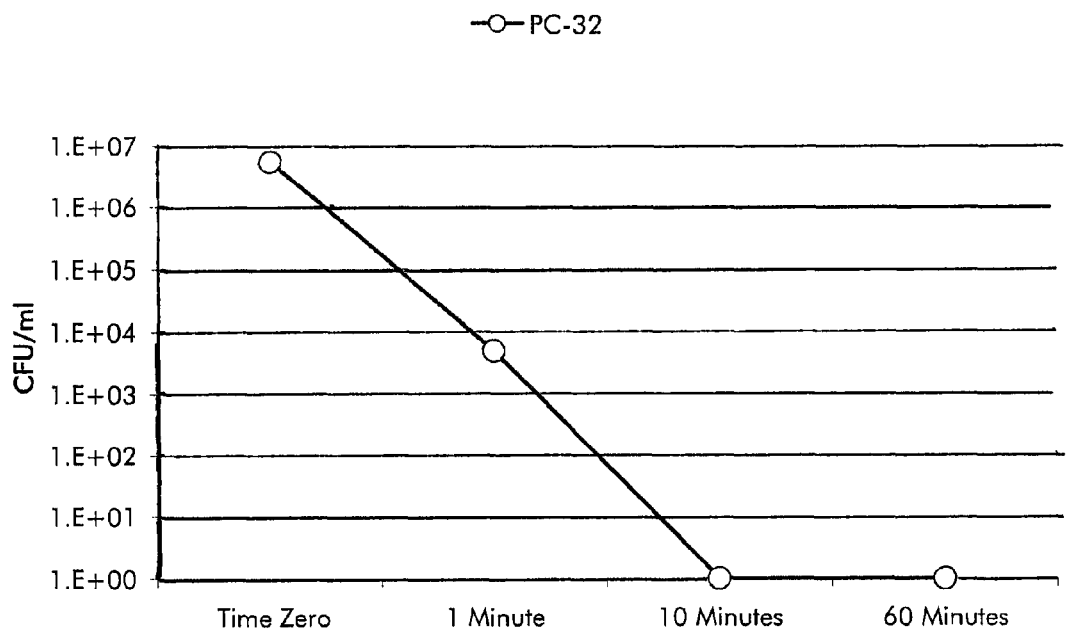
FIG. 2 shows results from a suspension time kill testing the liquid crystal mixture of the present invention against *S. aureus*.

It is to be understood that the figures and descriptions of the present invention have been simplified to illustrate elements that are relevant for a clear understanding of the invention, while eliminating, for purposes of clarity, other elements that may be well known. The detailed description will be provided herein below with reference to the attached drawings.

The present invention includes a method of manufacturing a liquid crystal mixture that includes 1) at least one polyhydric alcohol and/or its oligomers and esters with 2) at least one monoglyceride or fatty acid ester; and 3) an alkali reactant. The mixture may be manufactured without the addition of water and displays improved solubility and stability over the native monoglyceride. The liquid crystal compositions of the present invention allow for the use of monoglycerides with medium length carbon chains (typically between $C_8$ and $C_{22}$ that are known in the art to be antibacterial) in finished products without sacrificing efficacy of function or product formulation stability. This ability is a significant improvement over the prior art where, specifically, use of medium chain monoglycerides typically requires emulsification schemes that may diminish or negate the antimicrobial efficacy of the monoglycerides. The present invention emphasizes the use of monoglycerides having a length of $C_8$-$C_{22}$, as those compounds are reported to have antimicrobial attributes. However, the present invention is equally applicable to various fatty acids, monoglycerides, diglycerides, and triglycerides and work not here reported has established that the carbon chain length does not constrain the applicability of the methods of the present invention to other compounds.

Within this application, "liquid crystal mixture" means a liquid crystal mixture formed by the preferred embodiment wherein at least one polyhydric alcohol is combined with at least one medium chain glycerol ester and at least one alkali reactant. The crystals are dynamic and the morphology thereof is determined by concentration of fatty acid ester, type of polyhydric alcohol used, and the temperature of the mixture.

A fatty acid ester is introduced to a polyhydric alcohol solvent and heated to a temperature above the melting point of the ester but below the condensation point of the solvent. A predetermined amount of reactant is added to this heated mixture resulting in the partial hydrolysis, also known as saponification, of the ester constituent and subsequently forms the ester salt thereof. Mixing these components results in a stable liquid crystalline mixture wherein the ester and ester salt are within a polyhydric alcohol solvent. In certain preferred embodiments, no water is added in the process.

Examples of fatty acid esters are glyceryl or glycerol monesters (monoglycerides) with carbon chain lengths of between $C_6$-$C_{32}$ including, but not limited to, glycerol monocaprylin, glycerol monocaprin, glycerol monolaurin, glycerol monostearate, etc. and mixtures thereof. Fatty acids include, but are not limited to butyric, isobutyric, succinic, caproic, adipic, caprylic, capric, lauric, myristic, palmitic, and stearic acids, and their monoglycerides and mono-, di- and triglycerides of fatty acids, fatty acid esters of carboxylic acids of at least 6 carbon atoms.

Examples of polyhydric alcohols include, but are not limited to, glycerol, diglycerol, triglycerol, tetraglycerol and polyglycerols having a higher degree of condensation, 1,3-butylene glycol, propylene glycol, dipropylene glycol, triethylene glycol, polyoxypropylene glyceryl ether, polyoxypropylene, glycol, trimethylolethane, and trimethylolpropane.

Examples of strong basic agents are alkali and alkaline-earth metal hydroxides, such as lithium, sodium, potassium, and calcium hydroxides; alkali and alkaline-earth metal alkoxides, such as sodium, potassium and magnesium methoxides, ethoxides, isopropoxides and tert-butoxides, and aluminium isopropoxide, preferably sodium hydroxide, potassium hydroxide, and sodium methoxide, with a particularly preferred example being potassium hydroxide.

Other materials may be added to the solution in order to provide for various desired end product characteristics. Other ingredients include but are not limited to essential oils and phytochemicals such as botanical extracts, short and/or long chain fatty acids, buffers, others esters, aldehydes, ketones, alcohols, and other active microbiocide ingredients.

In one of the preferred embodiments, the liquid crystal mixture is comprised of polyglycerol, propylene glycol, distilled glycerol monolaurate and potassium hydroxide. The general reaction carried out in a polyhydric alcohol solvent is:

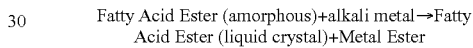
Fatty Acid Ester (amorphous)+alkali metal→Fatty Acid Ester (liquid crystal)+Metal Ester The polyglycerol component may comprise from about 10 to about 90 percent of the mixture by weight (wt/wt %) and be varied oligomers fractions. Glycerol may also be used in the methods of the present invention, though its use is accompanied by extended reaction temperatures and time. Polyglycerol mixtures of primarily di-glycerol and tri-glycerol display markedly reduced reaction times and allow for lower processing temperatures. The oligomer distribution of a given polyglycerol feedstock may be tightly distributed around a central oligomer, as is the case in polyglycerols intended for use in making food-grade esters, or a more even distribution of oligomers by weight over 4-6 species, as is the case in industrial grade polyols. The polyglycerol feedstock may or may not have color residues from high-temperature processing. Similarly, the polyglycerol feedstock may or may not have reactant residues remaining.

The present invention is particularly well-suited in reactions using food-grade triglycerol or diglycerol mixes, with little or no color and/or reactant residue. Vegetable-origin USP glycerin feedstock is also highly effective within the methods of the present invention.

Propylene and/or polypropylene glycol may be used at between about 10 and about 95% wt %/wt. Propylene glycol provides for reduced viscosity in the resulting product and provides for different product characteristics in the final mixture. USP, food-grade propylene glycol is particularly well-suited for use in the present invention.

Particularly preferred monoglycerides for use within the present invention are capric, caprylic, and lauric acid. The polyhydric solvents of polyglycerol (comprised of 2-9 glycerol oligomers) is also particularly well-suited for use in the present invention. In certain presently preferred embodiments, potassium hydroxide is used as the alkali reactant. The choices of raw materials are predicated upon the desired final product characteristics. Specific examples of the preparation of the liquid crystal composition follow.

Glycerol monolaurate raw material employed in the processes of the present invention may be of virtually any quality but is preferably distilled or in some other manner purified. For the present invention, glycerol monolaurate purified to a purity of greater than 90% monoglycerides, preferably greater than 95% is preferred. Lauric acid and glycerol monomer impurities up to 4% and 2%, respectively, are well tolerated within the context of the present invention, though higher levels of impurities may be used with appropriate modifications in procedures to compensate for the reaction of lauric acid with the alkali components of the system.

An alkaline reactant such as potassium hydroxide or sodium hydroxide may be added to the mix of polyglycerol and glycerol monolaurate, from amounts ranging from about 0.1 to about 4% wt %/wt dry weight of cation and hydroxyl. In practice, the reactant is added as an aqueous solution of between about 10% to about 80% reactant in water.

In one presently preferred embodiment of the present invention, the liquid crystal compositions are formed by combining propylene glycol, polyglycerol, and glycerol monolaurate and heating the mixture to temperatures between about 60° C. and about 230° C., in order to effectively melt the glycerol monolaurate and increase the reaction kinetics of saponification. Upon melting of the glycerol monolaurate, potassium hydroxide is added via methods well known in the art and the mixture is stirred. Upon stirring, the mixture goes from an initial cloudy, turbid phase to a clear phase within moments. Without being bound by theory, the inventors understand that upon the addition of the alkali reactant, a portion of the monoglyceride is converted to its ester salt form, thereby liberating glycerin and forming potassium laurate.

In an alternate method, the liquid crystal mixture of the present invention may be formed by combining all of the components at once and heating the mixture to between about 60° C. and about 230° C. in a single vessel.

Testing via liquid chromatography/mass spectrometry confirmed an approximate conversion of 4.2% of the glycerol monolaurate (GML) to potassium laurate. Without being bound to theory, it is believed that this conversion of GML to potassium laurate allows for the mixture to self-organize into an organized liquid crystalline structure.

Example 1

The methods of the present invention were used to prepare a liquid crystal mixture of three fatty acid esters with two polyhydric alcohols by partial hydrolyzation that was stable and antimicrobially active.

Propylene glycol and polyglycerol are combined at a ratio of 1:1. An aliquot of 40 grams of this polyhydric alcohol mixture is measured into a glass container. To this, 60 grams of a blend of glycerol monocaprate, glycerol monocaprylate, and glycerol monolaurate (5:5:40 respectively) is added directly to the polyhydric alcohol mixture. The entire mixture is heated to 110° C. To this heated mixture, approximately 4% by weight of a 45% aqueous solution of potassium hydroxide is added. The mixture is stirred and allowed to cool. The resultant mixture is clear and has low viscosity with a pH of approximately 9.2-9.5.

Example 1 shows high solubility in water, up to 80%, without the need for emulsification. Light polarized microscopy and laser diffraction confirmed the presence of liquid crystals in the sample.

Example 2

The methods of the present invention were employed to prepare a liquid crystal mixture of one fatty acid ester and two polyhydric alcohols by partial hydrolyzation to that was stable and antimicrobially active.

Propylene glycol and polyglycerol are combined at a ratio of 1:1. An aliquot of 40 grams of this polyhydric alcohol mixture is measured into a glass container. To this, 60 grams of glycerol monolaurate is added directly to the polyhydric alcohol mixture. The entire mixture is heated to 110° C. To this heated mixture, approximately 4% by weight of a 45% potassium hydroxide aqueous solution is added. The mixture is stirred and allowed to cool. The resultant mixture is clear and has low viscosity with a pH of approximately 9.2-9.5.

The resultant product of Example 2 is soluble in aqueous solutions and light polarized microscopy and laser diffraction confirmed the presence of liquid crystals in the samples.

Example 3

The methods of the present invention were used to prepare a concentrated glycerol monolaurate and a polyhydric alcohol liquid crystal mixture by partial hydrolyzation to creation a stable antimicrobial composition.

An aliquot of 40 grams of polyglycerol is mixed with 60 grams of glycerol monolaurate. This mixture is heated to 125° C. Potassium hydroxide (45% in an aqueous solution) is added to the mixture at 1.2 grams KOH (aq) per 20 grams of glycerol monolaurate. This mixture is then stirred with medium sheer for five minutes. As with all the samples, the mixture initially clouds, then clears upon mixing.

Testing of the mixture liquid chromatography/mass spectrometry confirmed a conversion of approximately 4.2% of the glycerol monolaurate to it potassium salt, potassium laurate. Resultant pH was recorded at 9.4. The mixture cooled to a white, opaque paste however no separation was observed. Warming the mixture to temperatures above 60° C. resulted in a clear solution with no observed separation.

Laser diffraction and polarized light microscopy showed that the mixture, in its molten state and paste states, was comprised of liquid crystals. Images of the liquid crystals are provided in FIG. 4.

Example 4

Preparation of a 5% glycerol fatty acid ester liquid crystal mixture. Propylene glycol and polyglycerol are combined at a ratio of 3:1. An aliquot of 30 grams of glycerol monolaurate is combined with 20 grams of the propylene glycol/polyglycerol mixture. The mixture is heated to 85° C. and 1.4 grams of a 45% potassium hydroxide solution is added for each 20 grams of glycerol monolaurate. The solution is mixed to obtain a clear, low viscosity mixture.

To this mixture, an additional 138 grams of polyglycerol and 412 grams of propylene glycol are added. The resultant solution is comprised of, by weight, approximately 4% glycerol monolaurate, 24% polyglycerol, 71% propylene glycol, and 1.2% potassium laurate. The mixture remains a clear, low viscosity solution at room temperature. Laser diffraction confirmed the presence of liquid crystals. Addition of this mixture to water results in a cloudy emulsion with no separation. Aqueous solutions of varied concentration resulted in increased viscosity dependent upon concentration of the liquid crystal mixture.

Example 5

The methods of the present invention were used to prepare mixtures of polyhydric/fatty acid liquid crystals in mineral oil. An aliquot of 24 grams of the mixture as prepared in Example 3 is heated to at least 60° C. wherein the paste becomes a clear liquid. An aliquot of 1 gram of cetyl alcohol (LIPO CHEM) is added and melted and mixed together with high shear. In a separate container, 75 grams of CARNATION mineral oil (SONNEBORN, Inc.) is heated to above 60° C. The cetyl alcohol/liquid crystal mixture is slowly added to the mineral oil with high shear mixing. The resulting product is a clear mixture of glycerol monolaurate and potassium laurate liquid crystals.

Example 6

An aliquot of 1.5 grams of the mixture of Example 2 is heated with 1.5 grams capric/caprylic triglycerides, 1 gram of cetyl alcohol, and 1 gram of oleyl alcohol to 60° C. and mixed vigorously. This solution is then added slowly to CARNATION mineral oil with mixing. The resultant mixture is clear and stable. Laser diffraction and light polarized microscopy verified the presence of liquid crystals. Antimicrobial testing showed complete inhibition of gram positive S. aureus at 0.1% dilutions.

Example 7

An aliquot of 20 grams of glycerol monolaurate is heated to 110° C. in the presence of 80 grams of propylene glycol. Once the glycerol monolaurate is melted, 1.4 grams of an aqueous mixture of 45% potassium hydroxide is added to the heated mixture and the entire mixture is stirred. The mixture is allowed to cool to room temperature. Laser diffraction confirmed the presence of liquid crystals.

Each of the liquid crystal compositions of the present invention may also be combined with synergists such as chelating agents, organic acids, inorganic acids, surfactants, phytochemicals, essential oils, quaternary ammonium compounds, halogen based antimicrobials, and other biocides, insecticides, fungicides, and herbicides to improve the antimicrobial activity of the mixture.

Tests of the antimicrobial activity of mixtures of polyglycerol and glycerol monolaurate demonstrate that such mixtures have similar efficacy to that of glycerol monolaurate alone. For example, glycerol monolaurate has a minimum inhibitory concentration (MIC) of 55 ppm when tested against *Staphylococcus aureus*. A composition of the present invention containing 18% glycerol monolaurate/82% polyglycerol oligomers and/or their esters displayed a MIC of 300 ppm when tested against *Staphylococcus aureus*—a value comparable to glycerol monolaurate alone.

Compositions of 2-90% of monoglyceride liquid crystal mixture generated by the methods of the present invention may be included in commercial formulations in concentrations up to about 60%. This high level of solubility stands in stark contrast to previously available commercial formulations which only had concentrations of glycerol monolaurate concentration up to 1-2%. This high level of solubility allows the compositions of the present invention to be incorporated into a wide variety of commercial formulations as described hereinbelow.

In some presently preferred embodiments of the present invention, the liquid crystal mixture is combined with a detergent or soap base. The surfactant base may be comprised of primary linear alkyl surfactants, primary aromatic surfactants, foam stabilizers, emulsifiers, ethanolamines, betains, etc. One example of a liquid soap or shampoo formulation is PEG-80 sorbitan laurate, sodium trideceth sulfate, PEG-150 distearate, lauroamphocarboxyglycinate, cocamidopropyle betaine, disodium laureth, sulfosuccinate, citric acid, liquid crystal mixture, fragrance, water, and sodium chloride. The surfactant blend may be prepared according to methods commonly known in the art and a measured amount of liquid crystal mixture from 5-20% wt/wt % may be added the surfactant blend with continuous mixing. Fragrance or essential oils may also be added. Water may be added at approximately 40% wt/wt %. Sodium chloride may be used to adjust for viscosity.

Another example of a liquid soap or detergent composition is ammonium lauryl sulfate, lauryl sulfate, ammonium laureth sulfate, ammonium xylene sulfonate, cocamide monoethanolamine, polysorbate-40, liquid crystal mixture, the essential oils of tea tree, lemon grass, and lavender, water, gluconate, and sodium chloride.

In another presently preferred embodiment of the present invention, the liquid crystal mixture may be incorporated into a viscous gel solution. Said solution is comprised of water, acid reactive thickening agent or polymer, setting agent, emulsifiers, emollients, and water. A specific example of a clear gel solution comprises sodium acrylate/acryloyldimethyl taurate copolymer, isohexadecane, polysorbate 80, cyclomethicone dimethicone crosspolymer, liquid crystal mixture, water, denatured ethanol, propylene glycol, and fragrance.

Another example of a clear gel solution containing the liquid crystal mixture is sodium polyacrylate, butylene glycol, PVM/MA copolymer, hydroxypropyl cellulose, glycerin, propylene glycol, liquid crystal mixture, ethanol, and fragrance.

In another presently preferred embodiment of the present invention, blended liquid crystal mixtures, at various concentrations, are mixed with lipid petrochemicals such as petrolatum, petroleum jelly or other. The liquid crystal mixture may be blended 20% by weight with 80% by weight petroleum jelly or petrolatum resulting in a viscous, antimicrobial lubricant and or emollient product. The liquid crystal mixtures of the present invention may also be mixed with nonpetro waxes such as oleo chemical, i.e. soybean oil based or with a combination of both.

In other presently preferred embodiments of the present invention, liquid crystal mixtures are combined with cosmetic grade waxes to provide for cosmetic or personal care products such as pressed cosmetics and lip treatments. Said liquid crystal mixture is combined at a weight percent from about 1 to about 50% with waxes of soy, red palm, or other botanical sources.

In other presently preferred embodiments of the present invention, liquid crystal mixtures are combined with sterile dressing preparations for health care applications including but not limited to hospital bedding, patient garments, scrubs, and other such articles.

In other presently preferred embodiments of the present invention, the liquid crystal mixtures are provided in dentifrice preparations as an active or inert ingredient including, but not limited to a preservative, emollient, antimicrobial, or other such formulation.

In other presently preferred embodiments of the present invention, the liquid crystal mixtures are provided in food preparations an active or inert ingredient including, but not limited to a preservative, thickener, antimicrobial, or other such component.

In other presently preferred embodiments of the present invention, the liquid crystal mixtures are aerosolized with propylene glycol and/or triethylene glycol to be used as an air sanitizer.

In other presently preferred embodiments of the present invention, the liquid crystal mixtures are added to drilling fluids or muds to act as a preservative and biocide for petroleum/natural gas drilling in order to inhibit/kill sulfur-reducing bacteria and gel-degrading bacteria.

In other presently preferred embodiments of the present invention, the liquid crystal mixtures are used in veterinary applications for live stock and domestic antimicrobial treatments and inhibition. One such application is the addition of liquid crystal mixtures to food to inhibit the growth the of *Clostridium difficile* in reptiles. Another application is the application of liquid crystal mixtures to physical surfaces in kennels and veterinary hospitals.

Nothing in the above description is meant to limit the present invention to any specific chemical components or any particular final formulation. Many chemical substitutions are contemplated within the scope of the present invention and will be apparent to those skilled in the art. The embodiments described herein were presented by way of example only and should not be used to limit the scope of the invention.

We claim:

1. A method of making a composition comprising the steps of:
   combining at least one fatty acid ester with at least one polyhydric alcohol;
   heating said combination to a temperature greater than a melting point of said fatty acid ester;
   adding an amount of alkaline reactant such that a portion of said fatty acid ester is saponified to a resultant ester salt; and
   wherein said ester salt and/or said fatty acid ester is in the form of a stable, liquid crystal mixture.

2. The method of claim 1, wherein said at least one fatty acid ester is selected from the group consisting of one mono-, di-, or triglyceride thereof that is a saturated fatty acid having a carbon chain with a number of carbon atoms numbering between 4 and 28 carbon atoms.

3. The method of claim 2, wherein said at least one monoglyceride is selected from at least one of 2,3-dihydroxypropyl decanoate, 2,3-dihydroxypropyl decanoate, 2,3-dihydroxypropyl dodecanoate, 2,3-dihydroxypropyl tetradecanoate, and 2,3-dihydroxypropyl hexadecanoate.

4. The method of claim 1, wherein said at least one fatty acid ester is comprised of glycerol monolaurate, glycerol monocaprate, and glycerol monocaprylate; said at least one polyhydric alcohol is comprised of at least one of propylene glycol and glycerol, diglycerol, triglycerol, tetraglycerol, pentaglycerol, hexaglycerol, heptaglycerol, octaglycerol, and pentalgycerol, further wherein and said alkali reactant is comprised of potassium hydroxide.

5. The method of claim 1, wherein said at least one polyhydric alcohol is selected from the group consisting of glycerin, diglycerine, 1,3-butylene glycol, propylene glycol, polypropylene glycol, polyoxypropylene glyceryl ether, and polyoxypropylene diglyceryl ether, neopentyl glycol, trimethylolethane, trimethylolpropane, glycerol, diglycerol, triglycerol, propylene glycol, dipropylene glycol, tripropylene glycol, tetraglycerol, pentaglycerol, hexaglycerol, heptaglycerol, and polyglycerols having a carbon chain length of greater than seven.

6. The method of claim 1, wherein said alkaline reactant is selected from the group consisting of sodium hydroxide, potassium hydroxide, lithium hydroxide, or cesium hydroxide, alkali metal hydroxide, and alkaline-earth metal hydroxide.

7. The method of claim 1, wherein said temperature is between about 55° C. and about 250° C.

8. The method of claim 1, wherein:
   said fatty acid ester comprises approximately 2-98% wt/wt % of said composition;
   said polyhydric alcohol comprises approximately 2-85% wt/wt % of said composition;
   said resultant ester salt comprises approximately 3-8% wt %/wt of said composition;
   free glycerine comprises approximately 0.1-5% wt %/wt of said composition; and
   water comprises less than 1% wt %/wt of said composition.

9. The method of claim 1, wherein said resultant composition is a biologically active antimicrobial mixture or a preservative.

10. A composition comprised of at least one fatty acid ester, at least one polyhydric alcohol, and an ester salt of monoglyceride, wherein said at least one fatty acid ester and/or said ester salt of a monoglyceride is in the form of a liquid crystal.

11. The composition of claim 10, wherein said at least one fatty acid ester is selected from the group consisting a saturated fatty acid having a carbon chain with a number of carbon atoms between 4 and 28, and mono-, di-, or triglycerides thereof.

12. The composition of claim 10, wherein said at least one fatty acid ester is selected from the group consisting of butyric, isobutyric, succinic, caproic, adipic, caprylic, capric, lauric, myristic, palmitic, and stearic acids, and their monoglycerides.

13. The composition of claim 10, wherein said at least one fatty acid ester is a monoglyceride, further wherein said monoglyceride is selected from the group consisting of 2,3-dihydroxypropyl decanoate, 2,3-dihydroxypropyl decanoate, 2,3-dihydroxypropyl dodecanoate, 2,3-dihydroxypropyl tetradecanoate, 2,3-dihydroxypropyl hexadecanoate, glycerol monolaurate, glycerol monocaprate, and glycerol monocaprylate.

14. The composition of claim 10, wherein said at least one polyhydric alcohol is selected from the group consisting of glycerin, diglycerine, 1,3-butylene glycol, propylene glycol, polypropylene glycol, polyoxypropylene glyceryl ether, and polyoxypropylene diglyceryl ether, neopentyl glycol, trimethylolethane, trimethylolpropane, triglycerol, tetraglycerol, and other polyglycerols having higher carbon chains.

15. The composition of claim 10, wherein said composition is essentially free of water.

16. The composition of claim 10, wherein said composition displays antimicrobial properties.

17. The composition of claim 10, wherein said composition is soluble in aqueous formulations.

18. The composition of claim 10, wherein said ester salt is an ester salt of potassium, magnesium, or sodium.

* * * * *